United States Patent [19]
Cook et al.

[11] Patent Number: 6,043,235
[45] Date of Patent: Mar. 28, 2000

[54] 11β-ARYL-17, 17-SPIROTHIOLANE-SUBSTITUTED STEROIDS

[75] Inventors: C. Edgar Cook, Staunton, Va.; Rupa S. Shetty, West Chester, Pa.; John A. Kepler, Raleigh, N.C.; David Y.-W. Lee, Cambridge, Mass.

[73] Assignee: Research Triangle Institute, Research Triangle Park, N.C.

[21] Appl. No.: 09/357,923

[22] Filed: Jul. 21, 1999

[51] Int. Cl.[7] ........................ A61K 31/58; C07J 33/00
[52] U.S. Cl. ............................ 514/173; 540/33
[58] Field of Search ................. 540/30; 514/173

[56] References Cited

U.S. PATENT DOCUMENTS

| | | |
|---|---|---|
| 5,292,878 | 3/1994 | Hamersma et al. .................. 540/28 |
| 5,741,786 | 4/1998 | Hamersma et al. .................. 514/173 |

*Primary Examiner*—Jose' G. Dees
*Assistant Examiner*—Barbara Badio
*Attorney, Agent, or Firm*—Oblon, Spivak, McClelland, Maier & Neustadt, P.C.

[57] ABSTRACT

The invention is directed to 11β-aryl-17,17-spirothiolane substituted steroid compounds of formula (I) exhibiting binding to the progestin receptor.

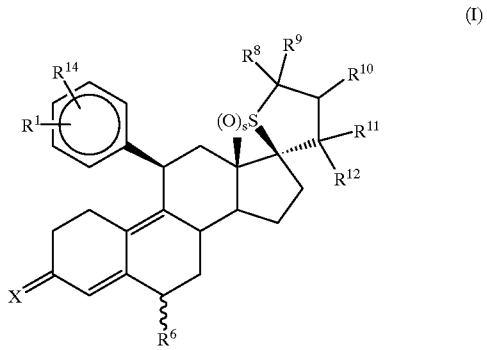

Also disclosed are methods of using and process of making the compounds.

10 Claims, 2 Drawing Sheets

11β-ARYL-17, 17-SPIROTHIOLANE-SUBSTITUTED STEROIDS

BACKGROUND OF THE INVENTION

The research leading to the present invention was supported in part with funds from NIH, NICHD Contract No. N01-HD-5-3238. Accordingly, the U.S. government may have certain rights to the invention.

FIELD OF THE INVENTION

The present invention is directed to 11β-aryl-17,17-spirothiolane-substituted steroid compounds, methods of making 11β-aryl-17,17-spirothiolane-substituted steroid compounds, and therapeutic treatments for the activity of progesterone using 11β-aryl-17,17-spirothiolane-substituted steroid compounds.

DISCUSSION OF THE BACKGROUND

Progesterone plays a major role in reproductive health and functioning, and its effects on, for example, the uterus, breast, cervix and hypothalamic-pituitary unit are well established. It also has extra-reproductive activities that are less well studied, such as effects on brain, immune system, vascular endothelial system and lipid metabolism. Given this wide array of effects, it is apparent that compounds which mimic some of the effects of progesterone (agonists), antagonize these effects (antagonists) or exhibit mixed effects (partial agonists or mixed agonist/antagonist) can be useful in a variety of diseases and conditions.

Steroid hormones exert their effects in part by binding to intracellular receptors.

Compounds that bind to the appropriate receptors and are antagonists or partial agonists of the estrogenic and androgenic hormones have long been known, but it was not until around 1982 that the discovery of compounds that bind to the progesterone receptor and antagonize the effects of progesterone was announced. Since then, a number of such compounds have been reported in the scientific and patent literature and their effects in vitro, in animals and in humans have been studied. Although compounds such as estrogens and certain enzyme inhibitors can prevent the physiological effects of endogenous progesterone, in this discussion "antiprogestin" is confined to those compounds that bind to the progestin receptor.

Information indicating that antiprogestins would be effective in a number of medical conditions is now available. This information has been summarized in a report from the Institute of Medicine (Donaldson, Molly S.; Dorflinger, L.; Brown, Sarah S.; Benet, Leslie Z., Editors, Clinical Applications of Mifepristone (RU 486) and Other Antiprogestins, Committee on Antiprogestins: Assessing the Science, Institute of Medicine, National Academy Press, 1993). In view of the pivotal role that progesterone plays in reproduction, it is not surprising that antiprogestins could play a part in fertility control, including contraception (long-term and emergency or post-coital), menses induction and medical termination of pregnancy, but there are many other potential uses that have been supported by small clinical or preclinical studies. Among these are the following:

1. Labor and delivery—antiprogestins may be used for cervical ripening prior to labor induction such as at term or when labor must be induced due to fetal death. They may also be used to help induce labor in term or post-term pregnancies.

2. Treatment of uterine leiomyomas (fibroids)—these non-malignant tumors may affect up to 20% of women over 30 years old and are one of the most common reasons for surgery in women during their reproductive years. Hysterectomy, the common treatment for persistent symptoms, of course results in sterility.

3. Treatment of endometriosis—this common (5 to 15% incidence, much larger in infertile women) and often painful condition is now treated with drugs such as danazol or gonadotrophin-releasing hormone analogs that have significant side-effects, or must be dealt with surgically.

4. Cancers, particularly breast cancers—the presence of progestin receptors in many breast cancers has suggested the use of antiprogestins in treating metatstatic cancer or in prevention of recurrence or initial development of cancer.

5. Other tumors such as meningiomas—these brain membrane tumors, although non-malignant, result in death of the patient and nonsurgical treatments are lacking.

6. Male contraception—antiprogestins can interfere with sperm viability, although whether this is an antiprogestational effect or not is controversial, as it may relate to the antiglucocorticoid activity of such compounds.

7. Antiestrogenic effects—at least some antiprogestins oppose the action of estrogens in certain tests, but apparently through a mechanism that does not involve classical hormone receptors. This opens a variety of possibilities for their medical use.

8. Antiglucocorticoid effects—this is a common side-effect of antiprogestins, which can be useful in some instances, such as the treatment of Cushing's syndrome, and could play a role in immune disorders, for example. In other instances it is desirable to minimize such effects.

9. Hormone replacement therapy—the ability to antagonize the actions of progestins is valuable for use in this area.

The effects and uses of progesterone agonists have been well documented. In addition, it has been recently shown that certain compounds structurally related to the known antiprogestins have strong agonist-like activity in certain biological systems (e.g., the classical progestin effects in the estrogen-primed immature rabbit uterus; cf. C. E. Cook et al., Life Sciences, 52, 155–162 (1993)). Such compounds are partial agonists in human cell-derived receptor systems, where they bind to a site distinct from both the progestin and antiprogestin sites (Wagner et al., Proc. Natl. Acad. Sci., 93, 8739–8744 (1996)). Furthermore the interaction of the receptor/drug complex with the genome can vary from class to class of antiprogestins—either binding to the genome may occur with no transcriptional result or the antiprogestin may prevent binding of the complex to the genome. Thus the general class of antiprogestins can have many subclasses, which may vary in their clinical profiles.

In spite of the clinical promise of antiprogestins, as of Mar. 1, 1999, there were no antiprogestin drugs marketed in the United States or many other countries. Only one antiprogestin drug is approved and available for clinical use anywhere in the world and that drug, mifepristone, is mainly used for medical termination of pregnancy. A number of factors are the cause of this situation, but certainly a need exists for new antiprogestational drugs that can be used for the conditions described above. It is one purpose of this invention to provide such drugs.

Generally antiprogestational activity has been associated with the presence of an 11β-aryl substituent on the steroid nucleus, together with a $\Delta^{4,9}$-3-ketone moiety. The earliest antiprogestins were substituted with a 17β-hydroxyl group and various 17α-substituents. (See for example, Teutsch et al. U.S. Pat. No. 4,386,085 Philibert et al. U.S. Pat. No.

4,477,445; Teutsch et al. U.S. Pat. No. 4,447,424; Cook, et al. U.S. Pat. Nos. 4,774,236 and 4,861,763. Then it was discovered that a 17β-acetyl-17α-acyloxy group could also generate antiprogestational effects (Cook et al. U.S. Pat. Nos. 4,954,490 and 5,073,548) and various permutations of these findings have been made as well. However, introduction of a 16α-ethyl group or a hydrogen substituent at the 17α-position in the 17β-acyl series of 11β-aryl compounds leads to agonist or partial agonist activity (C. E. Cook et al., *Life Sciences*, 52, 155–162 (1993)). Other reports in the area of antiprogestational compounds include Teutsch. et al. *Human Reproduction*. Jun. 9, 1994 (Supplement 1): 12–31 and Cook et al. *Human Reproduction*. Jun. 9, 1994 (Supplement 1):32–39. Thus changes in the D-ring of the steroid can result in unpredictable effects on the biological activity.

17-thio-substituted steroids have been reported in the literature. (e.g. Smith et al. *Journal Biological Chemistry*. 1974; 249(18):5924–5932; Varma U.S. Pat. No. 4,481,144; and Varma et al., U.S. Pat. No. 4,529,548.

It can be seen that the 17β-position of already known antiprogestins has been characterized by substitution with a carbon or an oxygen atom. No reports have been made of the effect of thio substituents such as 17,17-spirothiolanes in the 17β-position of 11β-aryl steroids on their hormonal or antihormonal activity. Until the current invention there existed no methods for their synthesis. No 17,17-spirothiolane steroids have been found in either the general chemical literature or in patents. The prior art thus does not permit a prediction regarding the activity of such compounds. One novel feature of the present invention is the finding that a spiro[17,17'-2'-thiolane] in 11β-aryl steroids result in compounds with good binding to the progestin receptor.

It is therefore the purpose of the present invention to provide novel and potent progestin receptor response modulators, to provide methods for their medical use in mammals, including humans, and to provide methods for their synthesis.

SUMMARY OF THE INVENTION

Accordingly, one embodiment of the present invention is directed to 17,17-spirothiolane steroid compounds with 11β-aryl substitution.

Another embodiment of the present invention is a method of synthesizing 17,17-spirothiolane steroid compounds with 11β-aryl substitution.

Another embodiment of the present invention is a method of modulating the effects of progestin by administering 17,17-spirothiolane steroid compounds with 11β-aryl substitution.

These and other objects of the present invention are made possible by 17,17-spirothiolane steroid compounds with 11β-aryl substitution of structure (I)

wherein s is an integer from 0 to 2;

$R^1$ is 4-$(R^2R^3N(O)_r)$-, where r is 0 or 1 and $R^2$ and $R^3$ are each independently H, $C_{1-6}$ alkyl, $C_{3-8}$ cycloalkyl, $C_{2-6}$ alkenyl or $C_{2-6}$ alkynyl, any of which may be optionally substituted; or where q is 0 or 1 and Y is —$(CH_2)_m$- where m is an integer of 0 to 5, or Y is —$(CH_2)_n$-Z—$(CH_2)_p$- where n is an integer of 0 to 2, p is an integer of 0 to 2 and Z is a heteroatom (optionally substituted) and where the methylene groups in both cases may be optionally substituted; or $R^1$ is 4-halo-, 4-HO—, 4-$CF_3SO_2O$—, 4-$CH_3O$—, 4-$CH_3S$—, 4-$CH_3S(O)$—, 4-$CH_3S(O)_2$-, 4-$CH_3CO$—, 4-$CH_3CH(OH)$—, 4-N≡C—, 4-HC≡C—, 4-$C_6H_5C$≡C—, 4-$H_2C$=CH—, 4-$C_2H_5$-, 4-MeC(=$CH_2$)—, 4-$C_6H_5$, 4-(N-imidazolyl)-, 4-(N-pyrrolyl)-, 4-(2'-furyl), 4-(3'-furyl)-, 4-(2'-thiophenyl), 4-(3'-thiophenyl)-, 4-(2'-pyridyl), 4-(3'-pyridyl), 4-(4'-pyridyl)-, 4-(2'-thiazolyl)-, 4-(2'-N-methylimidazolyl)-, or 4-(5'-pyrimidinyl)-;

$R^{14}$ is H or halo; or

$R^1$ and $R^{14}$ combine to form a ring where W is CH, $CH_2$, N, NH, O, or S, and $R^4$ is H, $CH_3$, or $C_2H_5$;

X is O or $NOR^5$, where $R^5$ is H or $C_{1-6}$ alkyl, $C_{3-8}$ cycloalkyl, $C_{2-6}$ alkenyl, $C_{2-6}$ alkynyl, $C_{6-12}$ aryl, or heteroaryl, any of which may be optionally substituted; or X is (H,H), (H,OH) or X is (H,OSi($C_{1-6}$-alkyl)$_3$) or X is (H,OCOR$^5$), where $R^5$ is $C_{1-6}$ alkyl, $C_{3-8}$ cycloalkyl, $C_{2-6}$ alkenyl, $C_{2-6}$ alkynyl, $C_{6-12}$ aryl, aralkyl, aralkenyl, aralkynyl, heteroaryl, heteroaralkyl, heteroaralkenyl or heteroaralkynyl, any of which may be optionally substituted; or X is where Y is —$(CH_2)_m$- where m is an integer of 0 to 3, or Y is —$(CH_2)_n$-Z—$(CH_2)_p$- where n is an integer of 0 to 2, p is an integer of 0 to 2 and Z is a heteroatom (optionally substituted) or Z is a carbon atom substituted with one or two lower alkyl groups;

$R^6$ is H, $C_{1-6}$ alkyl, or halogen;

$R^8$ and $R^9$ are individually H, $C_{1-18}$ alkyl, $C_{2-18}$ alkenyl, $C_{2-18}$ alkynyl, $C_{4-8}$cycloalkyl, $C_{6-12}$ aryl, aralkyl, aralkenyl or aralkynyl, heteroaryl, heteroaralkyl, heteroaralkenyl or heteroaralkynyl, any of which may be optionally substituted; and $R^{10}$ is H, $C_{1-18}$ alkyl, $C_{2-18}$ alkenyl, $C_{2-18}$ alkynyl, $C_{4-8}$ cycloalkyl, $C_{6-12}$ aryl, aralkyl, aralkenyl or aralkynyl, heteroaryl, heteroaralkyl, heteroaralkenyl or heteroaralkynyl, any of which may be optionally substituted; and $R^{11}$ and $R^{12}$ are =$CH_2$ or $R^{11}$ and $R^{12}$ are each H; and pharmaceutically acceptable salts thereof.

These and other objects of the present invention are made possible by the discovery that 11β-aryl-17,17-spirothiolane-substituted steroid compounds exhibit exceptional binding to the progesterone receptor.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Heteroatom means oxygen, nitrogen, sulfur, silicon or boron.

Halogen means fluorine, chlorine, bromine or iodine and halo means fluoro, chloro, bromo or iodo.

Aralkyl, aralkenyl, or aralkynyl means a $C_{1-6}$ alkyl, $C_{2-6}$ alkenyl or $C_{2-6}$ alkynyl group bearing an aryl substituent.

Lower alkyl means a $C_{1-6}$ alkyl group.

Heteroaryl means a unit of 5 to 12 non-hydrogen atoms consisting of one or more cyclic structures that may be fused or linked together, which contain 1 to 5 heteroatoms and which are generally accepted by those skilled in the art as having aromatic electronic character.

Heteroaralkyl, heteroaralkenyl, or heteroaralkynyl means a $C_{1-6}$ alkyl, $C_{2-6}$ alkenyl or $C_{2-6}$ alkynyl group bearing a heteroaryl substituent.

"Optionally substituted" means unsubstituted or substituted by replacement of a hydrogen atom with one or more heteroatom(s) and/or halogens and/or alkyl groups of 1 to 6 carbon atoms and/or alkenyl and/or alkynyl groups of 2 to 6 carbon atoms and/or cycloalkyl groups of 3 to 8 carbon atoms and/or aryl groups of 6 to 12 carbon atoms and/or heteroaryl groups, and in which the alkyl, alkenyl, alkynyl, cycloalkyl, aryl or heteroaryl group may be further substituted with one or more heteroatoms and/or halogens. Where their valency permits, heteroatoms may be substituted either within the carbon chain or by attachment to it by single or double bonds. For example, —$CH_2$—$CH_2$—CH=O, —$CH_2$(C=O)—$CH_3$, —$CH_2$—$CH_2$—O—$CH_3$, —$CH_2$—$CH_2$—$CH_2OH$, $CH_3$—$CH_2$—$CH_2O$—, $CH_2$—$CH_2$—C(=O)—$NH_2$, $CH_3$—$CH_2$—C(O)—NH— and $CF_3$—C≡—C— all fall within this definition.

In all cases where valency and steric considerations permit, alkyl, alkenyl, alkynyl and cycloalkyl groups may contain additional double or triple bonds and/or branched chains.

The structure of formula I is illustrated as a single enantiomer, however it will be appreciated by those of ordinary skill in the art that the present invention is directed to both enantiomeric forms. Those of ordinary skill in the art will also appreciate that enrichment in one enantiomeric form can be achieved by conventional methods known to those of ordinary skill in the art, such as by chromatography, crystallization, diastereomeric separation or starting from optically enriched starting materials. In a preferred embodiment the enantiomeric ratio will be 5:1, preferably 10:1, more preferably 15:1 and even more preferably greater than 20:1. In a preferred embodiment, the enriched enantiomer has the same absolute stereochemistry at $C_{13}$ as the d rotatory enantiomer of β-estradiol.

In all cases the sulfoxide group R'R"SO includes either of the two pure epimers as well as mixtures of the two epimers.

In all cases $R^6$ may be either alpha (α) or beta (β) to the aromatic ring

The above-identified compounds of formula I specifically include compounds which are substituted on the A ring at the 3-position with two hydrogen atoms. These compounds are believed to undergo oxidation in vivo to the corresponding carbonyl compound.

In a preferred embodiment, the present invention is directed to 17, 17 spirothiolane compounds of formula I wherein:

s is an integer from 0 to 2;

$R^1$—Ph is 4-aminophenyl, 4-(N-methylamino)phenyl, 4-(N,N-dimethylamino)phenyl, 4-(N-piperidino)phenyl, 4-(N-pyrrolidino)phenyl, 4-(N-morpholino)phenyl;

$R^{14}$ is H or $R^1$ and $R^{14}$—Ph is 1-methylindol-5-yl or 1-methyl-2,3-dihydroindol-5-yl;

X is O, NOH, or $NOCH_3$;

$R^6$ is H, $CH_3$, F or Cl;

$R^8$ is H, $CH_3$, or $C_6H_5$;

$R^9$ is H, $CH_3$, or $C_6H_5$;.

$R^{10}$ is H, $CH_3$, or $C_6H_5$; and $R^{11}$ and $R^{12}$ are each H.

The present invention is also directed to the following specific compounds:

11β-(4-N-methylamino)phenyl)-spiro[estra-4,9-diene-17β,2'-thiolane]-3-one;

11β-(4-(N,N-dimethylamino)phenyl)-spiro[estra-4,9-diene-17β,2'-thiolane]-3-one;

11β-(4-(N-piperidino)phenyl)-spiro[estra-4,9-diene-17β,2'-thiolane]-3-one;

11β-(4-(N-pyrrolidino)phenyl)-spiro[estra-4,9-diene-17β,2'-thiolane]-3-one;

11β-(4-(N-morpholino)phenyl)-spiro[estra-4,9-diene-17β,2'-thiolane]-3-one;

11β-(4-(N-methylamino)phenyl)-2'-oxospiro[estra-4,9-diene-17β,2'-thiolane]-3-one;

11β-(4-(N,N-dimethylamino)phenyl)-2'-oxospiro[estra-4,9-diene-17β,2'-thiolane]-3-one;

11β-(4-(N-piperidino)phenyl)-2'-oxospiro[estra-4,9-diene-17β,2'-thiolane]-3-one;

11β-(4(N-pyrrolidino)phenyl)-2'-oxospiro[estra-4,9-diene-17β,2'-thiolane]-3-one;

11β-(4-(N-morpholino)phenyl)-2'-oxospiro[estra -4,9-diene-17β,2'-thiolane]-3-one;

11β-(4-(N-methylamino)phenyl)-2',2'-dioxospiro[estra-4,9-diene-17β,2'-thiolane]-3-one;

11β-(4-(N,N-dimethylamino)phenyl)-2',2 '-dioxospiro[estra-4,9-diene-17β,2'-thiolane]-3-one;

11β-(4-(N-piperidino)phenyl)-2',2'-dioxospiro[estra-4,9-diene-17β,2'-thiolane]-3-one;

11β-(4-(N-pyrrolidino)phenyl)-2',2'-dioxospiro[estra-4,9-diene-17β,2'-thiolane]-3-one;

11β-(4-(N-morpholino)phenyl)-2',2'-dioxospiro[estra-4,9-diene- 17β,2'-thiolane]-3-one.

The compounds of the present invention may also comprise a salt, especially a salt formed with an amine, when present. Suitable pharmaceutically acceptable salts are known to those of ordinary skill in the art and comprise carboxylates, sulfates, phosphates and halides.

Steroids having progestational, antiprogestational and/or antiglucocorticoid activity have use in the control of fertility in humans and non-human mammals such as primates, domestic pets and farm animals, and in the treatment of medical conditions in animals or humans in which these activities are beneficial. Thus they may be useful in the treatment of conditions such as fibroids, Cushing's syndrome, glaucoma, endometriosis, cervical ripening prior to delivery, hormone replacement therapy, premenstrual syndrome and cancer in addition to their use in the control of fertility and reproduction.

The compounds of the present invention may be administered by a variety of methods. Thus, those products of the invention that are active by the oral route may be administered in solutions, suspensions, emulsions, tablets, including sublingual and intrabuccal tablets, soft gelatin capsules, including solutions used in soft gelatin capsules, aqueous or oil suspensions, emulsions, pills, lozenges, troches, tablets, syrups or elixirs and the like. Products of the invention active on parenteral administration may be administered by depot injection, implants including Silastic™ and biodegradable implants, intramuscular and intravenous injections.

Compositions may be prepared according to any method known to the art for the manufacture of pharmaceutical compositions and such compositions may contain one or more agents selected from the group consisting of sweetening agents, flavoring agents, coloring agents and preserving agents. Tablets containing the active ingredient in admixture with nontoxic pharmaceutically acceptable excipients which are suitable for manufacture of tablets are acceptable. These excipients may be, for example, inert diluents, such as calcium carbonate, sodium carbonate, lactose, calcium phosphate or sodium phosphate granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropylethyl cellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension may also contain one or more preservatives such as ethyl or n-propyl p-hydroxybenzoate, one or more coloring agents, one or more flavoring agents and one or more sweetening agents, such as sucrose, aspartame or saccharin. Ophthalmic formulations, as is known in the art, will be adjusted for osmotic pressure.

Oil suspensions may be formulated by suspending the active ingredient in a vegetable oil, such as arachis oil, olive oil, sesame oil or coconut oil, or in a mineral oil such as liquid paraffin. The oil suspensions may contain a thickening agent, such as beeswax, hard paraffin or cetyl alcohol. Sweetening agents may be added to provide a palatable oral preparation. These compositions may be preserved by the addition of an antioxidant such as ascorbic acid.

Dispersible powders and granules of the invention suitable for preparation of an aqueous suspension by the addition of water may be formulated from the active ingredients in admixture with a dispersing, suspending and/or wetting agent, and one or more preservatives. Suitable dispersing or wetting agents and suspending agents are exemplified by those disclosed above. Additional excipients, for example sweetening, flavoring and coloring agents, may also be present.

The pharmaceutical composition of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a nontoxic parenterally acceptable diluent or solvent, such as a solution of 1,3-butanediol. Among the acceptable vehicles and solvents that may be employed are water and Ringer's solution, an isotonic sodium chloride. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Sterilization may be performed by conventional methods known to those of ordinary skill in the art such as by aseptic filtration, irradiation or terminal sterilization (e.g. autoclaving).

Aqueous formulations (i.e oil-in-water emulsions, syrups, elixers and injectable preparations) may be formulated to achieve the pH of optimum stability. The determination of the optimum pH may be performed by conventional methods known to those of ordinary skill in the art. Suitable buffers may also be used to maintain the pH of the formulation.

The compounds of this invention may also be administered in the form of suppositories for rectal administration of the drug. These compositions can be prepared by mixing the drug with a suitable nonirritating excipient which is solid at ordinary temperatures but liquid at the rectal temperatures and will therefore melt in the rectum to release the drug. Non-limiting examples of such materials are cocoa butter and polyethylene glycols.

They may also be administered by intranasal, intraocular, intravaginal, and intrarectal routes including suppositories, insufflation, powders and aerosol formulations.

Products of the invention which are preferably administered by the topical route may be administered as applicator sticks, solutions, suspensions, emulsions, gels, creams, ointments, pastes, jellies, paints, powders, and aerosols.

Products having anti-glucocorticoid activity are of particular value in pathological conditions characterized by excess endogenous glucocorticoid such as Cushing's syndrome, hirsutism and in particular when associated with the adrenogenital syndrome, ocular conditions associated with glucocorticoid excess such as glaucoma, stress symptoms associated with excess glucocorticoid secretion and the like.

Products having progestational activity are of particular value as progestational agents, ovulation inhibitors, menses regulators, contraceptive agents, agents for synchronization of fertile periods in cattle, and the like. When used for contraceptive purposes, they may conveniently be admixed with estrogenic agents, such as for example as ethynylestradiol or estradiol esters.

Products having anti-progestational activity are characterized by antagonizing the effects of progesterone. As such, they are of value in assisting in labor and delivery, in treatment of fibroids and endometriosis and in hormone replacement therapy.

The compounds of the invention may be used for control of fertility during the whole of the reproductive cycle. They are of particular value as postcoital contraceptives, for rendering the uterus inimical to implantation, and as "once a month" contraceptive agents. They may be used in conjunction with prostaglandins, oxytocics, estrogens and the like.

A further important utility for the products of the invention lies in their ability to slow down growth of hormone-dependent cancers. Such cancers include kidney, breast, endometrial, ovarian cancers, and prostate cancer which are characterized by possessing progesterone receptors and may be expected to respond to the products of this invention. Other utilities of anti-progestational agents include treatment of fibrocystic disease of the breast. Certain cancers and in particular melanomas may respond favorably to corticoid/anticorticoid therapy.

The compounds according to the present invention may be administered to any warm-blooded mammal such as humans, domestic pets, and farm animals. Domestic pets include dogs, cats, etc. Farm animals include cows, horses, pigs, sheep, goats, etc.

The amount of active ingredient that may be combined with a carrier material to produce a single dosage form will vary depending upon the disease treated, the mammalian species, and the particular mode of administration. A therapeutically effective amount may be determined by routine experimentation and by analogy from the amounts used to treat the same disease states with analogous steroid compounds. For example, a unit dose of the steroid may preferably contain between 0.1 milligram and 1 gram of the active ingredient. A more preferred unit dose is between 0.001 and 0.5 grams. For the specific treatment of endometriosis or fibroids an amount of 0.01 to 10 mg/kg of body weight, preferably from 0.1 to 3 mg/kg may be administered. Similar dosages may be used for the other therapeutic purposes of these compounds. Ordinarily the compounds may be administered daily 1 to 4 times per day, preferably 1 to 2 times per day, but for uses such as for example in hormone replacement therapy, they may be administered in a cyclophasic regimen. In any case the frequency and timing of dosage will depend upon factors such as the half-life of the specific compound in the body, the dosage formulation and the route of administration. It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those of skill in the art.

Such compounds are useful in the treatment of endometriosis, uterine leiomyomas (fibroids) and certain cancers and tumors, in hormone replacement therapy as well as in the control of various steps in reproduction and fertility, such as contraception. A more detailed description of the potential uses of such compounds is given in Donaldson, Molly S.; Dorflinger, L.; Brown, Sarah S.; Benet, Leslie Z., Editors, *Clinical Applications of Mifepristone (RU 486) and Other Antiprogestins*, Committee on Antiprogestins: Assessing the Science, Institute of Medicine, National Academy Press, 1993. They are also useful as intermediates for the synthesis of other steroids.

The present invention is also directed to a process of forming a $C_{17}$ cyclic spirothiolane of a steriod compound comprising reacting a $C_{17}$ thioketone with an allylic organometallic compound, such as an allylic Grignard or an allyic cuprate, followed by radical cyclization, such as induced by a radical initiator, such as AIBN. The formation of a $C_{17}$ thioketone from the corresponding $C_{17}$ ketone may be accomplished by conventional methods known to those of ordinary skill in the art, such as by treating the ketone with Lawesson's reagent. Oxidation of the cyclic sulfide to the corresponding cyclic sulfoxide or cyclic sulfone can be accomplished by conventional methods known to those of ordinary skill in the art, without undue experimentation, such as by treatment with $H_2O_2$. The addition and cyclization portions of the process are illustrated below:

where $R^8$–$R^{12}$ are as defined above and M is a metal cation.

Based in-part on this disclosure, the compounds of the present invention may be prepared by conventional methods known to those of ordinary skill in the art without undue experimentation.

General Methods.

Figure 1:
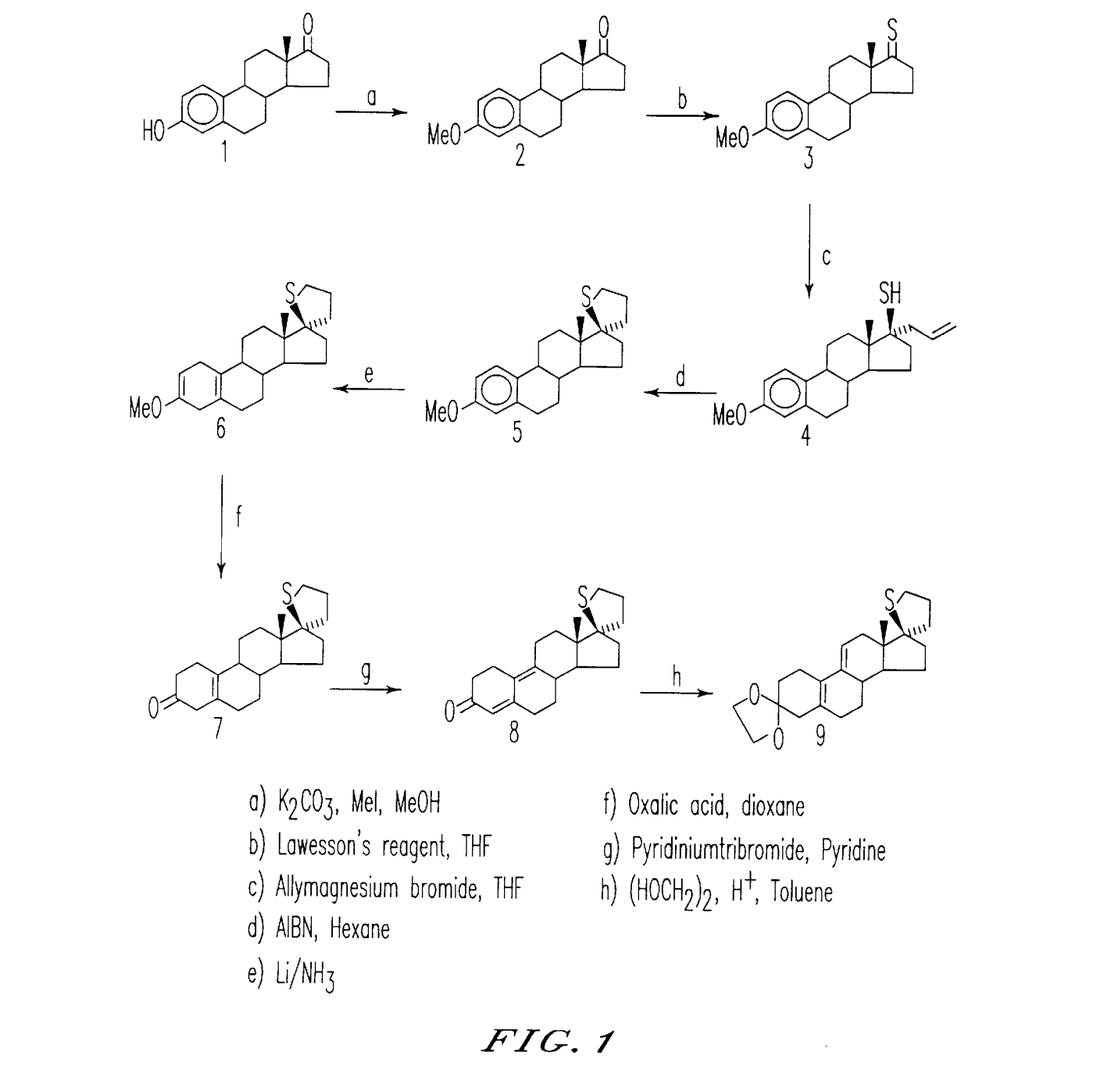
FIGS. 1 and 2 depict a reaction scheme to prepare 11β-aryl-17,17-spirothiolane-substituted steroid compounds according to the present invention.
Figure 2:
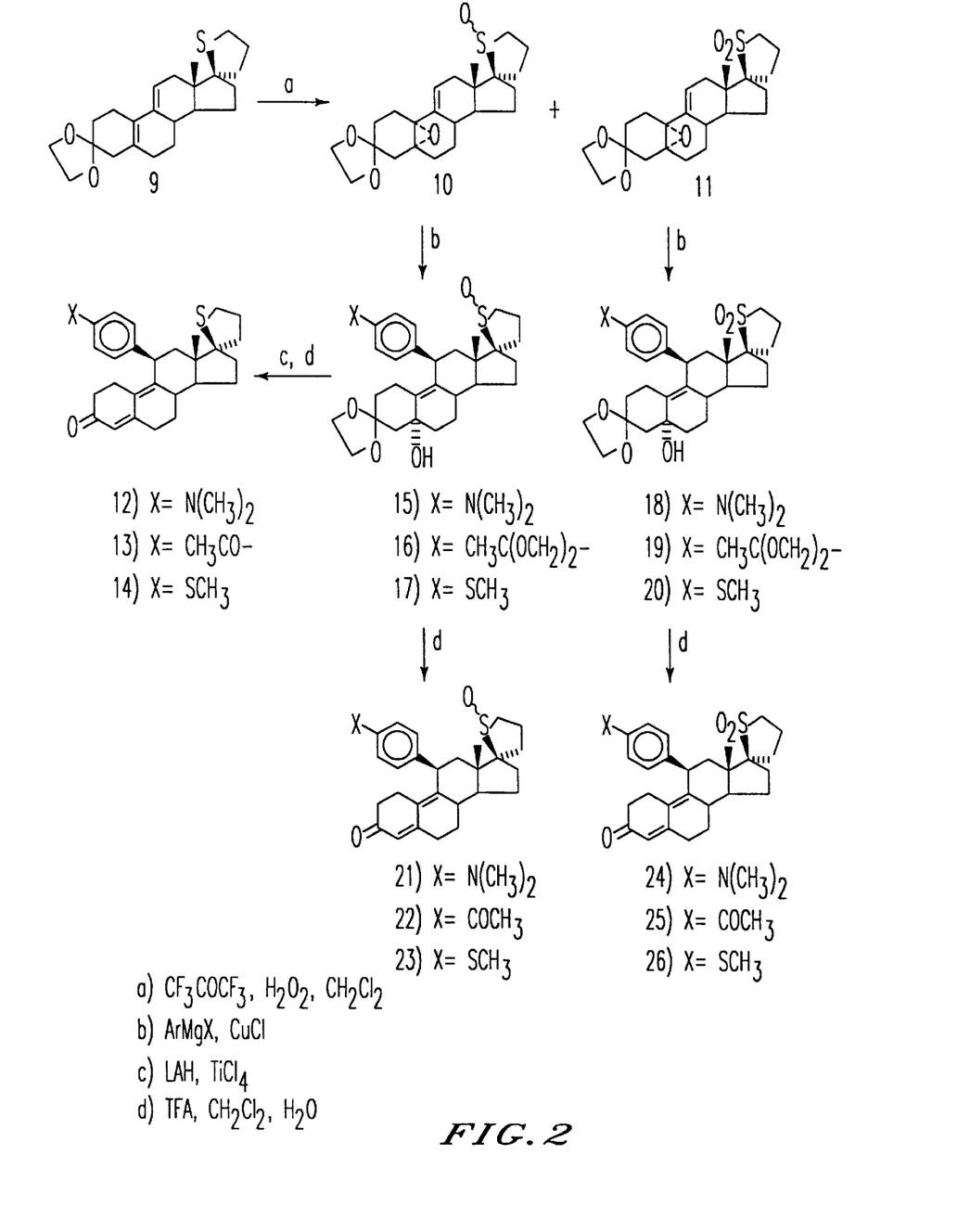

Compounds of this invention may be made according to the procedures outlined in Charts 1 and 2 and exemplified by the examples. To obtain the thione 3, estrone (1) is converted to its 3-methyl ether 2 by standard procedures. Reaction of 2 with Lawesson's reagent [2,4-bis(4-methoxyphenyl)-1,3-dithia-2,4-diphosphetane-2,4-disulfide] gives the 17-thione in 50–60% yield, together with recovery of 20–25% of the starting material. Treatment of the thione 3 with allyl magnesium bromide results in a high yield of the 17α-allyl-17β-mercapto compound 4. The procedure of J. Von Christjohannes et al. [Radical Cyclizations of Alkenyl-Substituted 4,5-Dihydro-1,3-thiazole-5-thiols. *Helv. Chim. Acta,* 72:838–846 (1989)] in which the reaction is carried out in the presence of cuprous iodide and worked up with dithiothreitol gives an 80% yield of 4. However, the reaction also proceeds well in the absence of cuprous iodide, in which case the use of dithiothreitol in the workup procedure is unnecessary. The thiol on subjection to radical cyclization conditions [azo-bis(isobutyronitrile) (AIBN) in refluxing hexane] gives greater than 90% conversion to the cyclic spirothiolane 5. Since the reaction occurs by a radical chain process, a low molar ratio of the radical initiator is often used in such reactions. However, experiments performed by varying the ratio of AIBN used showed that approximately an equimolar ratio of AIBN to thiol gives the best yields and conversion. In addition the reaction time needed to complete the conversion is lessened.

Reduction of the aromatic ring of 5 under Birch conditions gives enol ether 6 in good yield. The enol ether so obtained is subjected to oxalic acid hydrolysis, resulting in formation of β,γ-unsaturated ketone 7. On a large scale it was found that the product 7 was accompanied by the sulfoxide derivative of 7, possibly due to oxidation by peroxide impurities in the dioxane. This byproduct can easily be converted to the epoxide sulfoxide compound 10 (Chart 2) as described below for the conversion of compound 7 to 10. Thus the overall yield in this hydrolysis reaction is 91% of usable products. Treatment of ketone 7 with pyridinium tribromide in pyridine yields the 4,9-diene-3-ketone 8. This ketone is converted to the 5(10),9(11)-diene-3-ketal 9 by treatment with ethylene glycol in the presence of acid and then is subjected to epoxidation conditions with $H_2O_2$ (see Chart 2). Epoxidation is accompanied by oxidation of the sulfur atom to sulfoxide and/or sulfone. The degree of sulfur oxidation is dependent on the relative amount of $H_2O_2$ and the conditions used. Use of premixed epoxidation reagents, hexafluoroacetone trihydrate and hydrogen peroxide, in such an amount as to give an approximate 2.6:1 molar ratio of peroxide to the diene ketal 9 gives a 72% yield of the sulfoxide epoxide 10 together with a 22% yield of the sulfone epoxide 11. Increasing amounts of $H_2O_2$ results in more of the sulfone. The sulfoxide and sulfone are readily separable by chromatography.

Reaction of arylmagnesium bromide reagents with the sulfone epoxide 11 proceeds in good yields within a short time when a 15:5:1 ratio of Grignard reagent to CuCl to steroid is used. Acid hydrolysis and dehydration of the addition product 18 yields the dienone 24. Similar procedures lead to other sulfone analogs such as compounds 25 and 26.

The sulfoxide epoxide 10 on reaction with p-N,N-dimethylaminophenyl Grignard reagent in the presence of CuCl yields 76% of 11β-adduct 15. Acid hydrolysis of the adduct 15 with trifluoroacetic acid/water/$CH_2Cl_2$ gives sulfoxide dienone 21 in 70% yield as a mixture of epimers of the sulfoxide. The two epimers are separable on reverse phase HPLC.

The same reaction conditions can be employed to make other sulfoxide dienones such as 22 and 23, and the two isomers of the sulfoxides can be separated by preparative HPLC on a C-18 reverse phase column. The original oxidation to produce 10 creates a new asymmetric center at the sulfur atom and leads to a mixture of epimeric sulfoxides. These are carried through the reaction sequence and separated at the final product stage to give a major and a minor isomer.

Reduction of sulfoxide 15 by lithium aluminum hydride (LAH) and $TiCl_4$ [cf. the procedure of Drabowicz et al. *Synthesis,* 527–528 (1976)] readily leads to the sulfide. Acid hydrolysis and dehydration of the crude product leads to the dienone sulfide 12 in overall 50% yield. The same procedures can be used to make analogous compounds such as 13 and 14.

Various other procedures may be used to make the compounds of the invention, as will be apparent to those skilled in the art. For example, the ratio of the sulfoxide epimers may be controlled by the use of asymmetric reagents or by the size or structure of the oxidizing reagent.

Having generally described this invention, a further understanding can be obtained by reference to certain specific examples which are provided herein for purposes of illustration only and are not intended to be limiting unless otherwise specified.

General Procedures. Unless otherwise stated, reagent-grade chemicals were obtained from commercial sources and were used without further purification. Ether and tetrahydrofuran (THF) were freshly distilled from sodium benzophenone ketyl pair under nitrogen. All moisture- and air-sensitive reactions and reagent transfers were carried out under dry nitrogen or argon. Thin layer chromatography (TLC) was performed on EM Science precoated silica gel 60 F-254 plates. Compounds were normally visualized by UV light (254 nm) or para-anisaldehyde spray. Preparative column chromatography employed EM Science silica gel, 60Å (230–400 mesh). Solutions were concentrated by use of a rotoevaporator under water aspirator pressure at ambient temperature. Melting points were taken on a Mel-Temp II and are uncorrected. Unless otherwise noted, $^1$H NMR spectra were obtained at 250 MHz on a Bruker AC 250 spectrometer in CDCl$_3$ as solvent with tetramethylsilane (TMS) as internal standard. Chemical shifts are reported in units of ppm downfield from TMS. Mass spectra were normally obtained by electron impact at 70 eV on a Hewlett Packard 5989A instrument. Elemental analyses were performed by Atlantic Microlab Inc., Atlanta, Ga.

3-Methoxyestra-1,3,5(10)-trien-17-one (2).

Estrone (1, 100.0 g, 370 mmol) was dissolved in MeOH (1.5 L), followed by the addition of K$_2$CO$_3$ (300.0 g, 2.17 mol). MeI (310 mL, 4.98 mol) was added and the mixture stirred at room temperature for 70 h. The reaction mixture was concentrated in vacuo to remove some of the MeOH and was then poured into ice water forming a precipitate. The solid was collected and dried by partitioning into CH$_2$Cl$_2$. The organic layer was dried over MgSO$_4$, and the solvent was removed in vacuo to yield compound 2 (105.0 g) as white crystals in quantitative yield. $^1$H NMR (250 MHz, CDCl$_3$); δ 0.91 (s, 3, C-18 H), 3.78 (s, 3, MeO), 6.65 (s, 1, C-4 H), 6.72 (d, 1, J=8.57 Hz, C-2 H), 7.21 (d, 1, J=8.57 Hz, C-1 H).

3-Methoxyestra-1,3,5(1 0)-triene-1 7-thione (3).

Estrone methyl ether (2, 17.64 g, 62.2 mmol) was dissolved in 500 mL of dry tetrahydrofuran (THF) and a first portion of Lawesson's reagent (13 g, 32 mmol) was added. The reaction mixture containing suspended solid was heated to reflux for 18 h when all solids dissolved and the solution became salmon red. A second portion of Lawesson's reagent (13 g, 32 mmol) was added and heating continued at reflux temperature for another 18 h. Similarly, a third portion of Lawesson's reagent (13 g, 32 mmol) was added; and after being heated for 18 h, the reaction mixture was cooled and the THF evaporated to give a thick slurry. The slurry was dissolved in a minimum amount of CH$_2$Cl$_2$ and passed through a pad of silica gel to remove a polar by-product of Lawesson's reagent. The eluent was concentrated to afford a bright orange solid which was further purified by column chromatography on silica gel with EtOAc-Hexanes (1:3) as eluent to afford a bright orange solid product (10.5 g, 35 mmol) in 56% yield as the first fraction and then starting material (4 g, 14.0 mmol) in 23% recovery. Crude thione 3 can be further purified by crystallizing from boiling EtOAc, although after column purification it is pure enough for subsequent reactions. $^1$H NMR (250 MHz, CDCl$_3$) δ 0.94 (s, 3, C-S 8 CH$_3$), 3.78 (s, 3, —OCH$_3$), 6.64–6.75 (m, 2, ArH), 7.22 (d, J=10 Hz, 1 ArH); $^{13}$C NMR (250 MHz, CDCl$_3$) δ 273.3 (C=S).

17α-Allyl-3-methoxyestra-1,3,5(10)-triene-17β-thiol (4).

Method A. CuI (58.4 mg, 0.31 mmol) was suspended in 100 μL of tetrahydrofuran (THF) and cooled to 0° C. Allylmagnesium bromide solution (600 μL, 0.59 mmol) was added dropwise and the reaction mixture stirred vigorously for 30 min. Thione 3 (100 mg, 0.33 mmol) in 5 mL of THF was added dropwise to the reaction mixture at 0° C., followed by stirring for 3 h. Solid dithiothreitol (61.7 mg, 0.40 mmol) was added and the mixture was stirred for 30 min. The reaction mixture was filtered through a pad of Celite and silica gel and the filtrate concentrated to afford crude 3 (106 mg, 0.31 mmol) in 94% yield. The crude product was used in the next step. $^1$H NMR δ7.21 (d, 1 J=8.6 Hz, C-1 H), 6.63 (s, 1, C-4 H), 6.14–5.98 (m, 1, allyl-CH), 5.20–5.10 (m, 2, allyl-CH$_2$), 3.78 (s, 3, OMe), 1.00 (s, 3, C-18 H).

Method B. To 65 mL of a I M solution of allylmagnesium bromide under a nitrogen atmosphere at ambient temperature was added dropwise a solution of 15 g (50 mmol) of thione 3 dissolved in 150 mL of THF. After addition the mixture was stirred for 10 min. The reaction was quenched with saturated NH$_4$Cl solution and the mixture was extracted with EtOAc. The extracts were washed with water, followed by brine, and dried over anhydrous Na$_2$SO$_4$. After filtration through a small pad of silica gel, the filtrate was concentrated and the residue (16 g) used without further purification. $^1$H NMR equivalent to that above.

3-Methoxy-spiro[estra-1,3,5(10)-triene-17β,2'-thiolane] (5).

To a mixture of 17 g (49.7 mmol) of thiol 3 in 800 mL of hexane under an atmosphere of nitrogen was added 8.2 g (49.2 mmol) of AIBN. The reaction mixture was refluxed for 8 h and then filtered through silica gel, which was rinsed with ether. The solution was then concentrated and the crude product was used without further purification. Spiro compound 5 had the following properties: $^1$H NMR (250 MHz, CDCl$_3$), δ7.15 (d, 1, ArH), 6.55–6.66 ( m, 2, ArH), 3.70 (s, 3, OMe), 0.85 (s, 3, C-18 CH$_3$). MS m/z 342 (M+), 314, 267, 227, 186, 174, 147, 113, 79.

3-Methoxy-spiro[estra-2,5(10)-diene-17β,2'-thiolane] (6).

To 500 mL of condensed ammonia at −78° C. maintained under an atmosphere of nitrogen was added the spiro compound 5 (13.2 g, 38.6 mmol) in 1750 mL of THF and 75 mL of t-butanol. To this was added 0.8–1.0 g (133–147 equiv) of Li, and the mixture was stirred for 3 h at −78° C. The reaction mixture was quenched at −78° C. with methanol and then extracted with ethyl acetate. The extract was washed with saturated ammonium chloride solution followed by brine. The organic layer was dried over anhydrous sodium sulfate, filtered and concentrated. The crude product was used without purification. $^1$H NMR (250 MHz CDCl$_3$), δ0.93 (s, 3, C-18 CH$_3$), 3.55 (s, 3, OMe), 4.64 (s, 1, C-2 H).

Spiro[estra-5(10)-ene-17β,2'-thiolane]-3-one (7).

To the above enol ether 6 dissolved in 450 mL of dioxane was added 225 mL of water and 8.53 g of oxalic acid. The reaction mixture was stirred at room temperature overnight and then quenched with saturated NaHCO$_3$ solution. This mixture was then extracted with ethyl acetate. The organic layer was washed with water, followed by brine, and dried over anhydrous MgSO$_4$. The organic layer was filtered, concentrated, and chromatographed on silica gel with 2:1 hexane-EtOAc as eluent to give 10.9 g (86% yield) of 7. $^1$H NMR δ2.78 (ABq, 2, J=20 Hz, C-4 H), 1.14 (s, 3, C-18 H).

Spiro[estra-4,9-diene-17P,2'-thiolane]-3-one (8).

Enone 7 (9.2 g, 27.9 mmol) was dissolved in 100 mL of anhydrous pyridine. This solution was cooled to −20° C. and maintained under an inert atmosphere. A solution of 10.7 g (33.5 mmol) of pyridinium tribromide dissolved in 25 mL of pyridine was added dropwise to the solution of 7. The reaction mixture was slowly warmed to room temperature and stirred overnight. Water was added and the mixture was extracted with ethyl acetate. The organic layer was washed with dilute HCl solution and water, followed by brine, and dried over anhydrous MgSO$_4$. The organic layer was filtered, concentrated, and the crude product chromatographed on silica gel with 1:1.5 hexane-EtOAc as eluent to give 9.14 g (73% yield) of 8. $^1$H NMR δ5.68 (s, 1, C-4 H), 1.06 (s, 3, C-18 H).

3,3-[1,2-Ethanediylbis(oxy)]-spiro[estra-5(10),9(11)-diene-17β,2'-thiolane] (9).

To 108 mg (0.33 mmol) of diene ketone 8 dissolved in 10 mL of benzene was added 0.37 mL of ethylene glycol and a catalytic amount of p-TsOH. The reaction was heated at reflux for 2 h and then quenched with saturated NaHCO$_3$ solution. The reaction mixture was extracted with ethyl acetate. The organic layer was washed with water, followed by brine, and dried over anhydrous MgSO$_4$. The mixture was then filtered, concentrated, and chromatographed on silica gel with 10:1 hexane-EtOAc as eluent to give 113 mg (93% yield) of 9. $^1$H NMR δ5.61 (br s, 1, C-11 H), 3.99 (s, 4, (CH$_2$O)$_2$), 0.89 (s, 3, C-18 H).

3,3-[1,2-Ethanediylbis(oxy)]-1'-oxo-5,10α-oxido-spiro[estr-9(11)-ene-17β,2'-thiolane] (10).

To a solution of hexafluoroacetone trihydrate (3.72 mL, 26.7 mmol) in 26.5 mL of CH$_2$Cl$_2$ at −5° C. was added 1.98 mL (34.5 mmol) of 50% hydrogen peroxide. This mixture was maintained at −5° C. for 1 h. The solution of hexafluoroacetone-hydrogen peroxide was added to a solution of diene 9 (4.95 g, 13.3 mmol) in 14.3 mL of CH$_2$Cl$_2$ and 940 mg of Na$_2$HPO$_4$ at 0° C. The reaction mixture was allowed to slowly warm to room temperature and was stirred for another 7 h. The reaction was quenched with 5% Na$_2$SO$_3$ solution and was extracted with CH$_2$Cl$_2$; the organic extract was washed with water, followed by brine. The organic layer was dried over anhydrous MgSO$_4$, filtered, concentrated, and the crude product chromatographed. Elution with 3:6:1 hexane-EtOAc-MeOH gave 3.72 g (72% yield) of 10: $^1$H NMR δ6.04 (d, 1, J=2.4 Hz, C-11 H), 3.96–3.87 (m, 4, (CH$_2$O)$_2$), 2.99 (t, 2, J=7.4 Hz, J=8.5 Hz, C-5' H), 1.12 (s, 3, C-18 H).

11β-[4-(N,N-Dimethylamino)phenyl]-3,3-[1,2-ethanediylbis(oxy)]-1'-oxo-5α-hydroxy-spiro[estr-9-ene-17β,2'-thiolane] (15).

A solution of the Grignard reagent was prepared from 774 mg (3.87 mmol) of p-N,N-dimethylaminophenyl bromide and 45 mg (3.89 mmol) of Mg in 3.88 mL of THF. The Grignard reagent was cooled to −10° C. under an inert atmosphere. To the cooled solution of Grignard reagent was added 76.5 mg (0.77 mmol) of CuCl followed by 100 mg (0.26 mmol) of epoxide 10 in 1 mL of THF. The reaction was stirred at −10° C. for 30 min and then quenched with saturated NH$_4$Cl solution. The reaction mixture was extracted with EtOAc, washed twice with saturated NH$_4$Cl solution and dried over anhydrous Na$_2$SO$_4$. The EtOAc layer was filtered, concentrated, and chromatographed on silica gel with 2:1 EtOAc-hexane as eluent to give 99 mg (76% yield) of 15: $^1$H NMR δ7.07 (d, 2, J=8.6 Hz, ArH), 6.64 (d, 2, J=8.8 Hz, ArH), 4.40 (s, 1, C-5 OH), 4.24 (d, 1, J=6.0 Hz, C-11 H), 4.00–3.93 (m, 4, (CH$_2$O)$_2$), 2.90 (m, 1, C-S H), 2.89 (s, 6, N (CH$_3$)$_2$), 0.85 (s, 3, C-18 H, minor isomer), 0.68 (s, 3, C-18 H, major isomer).

11β-[4-(N,N-Dimethylamino)phenyl]-1'-oxo-spiro[estr-4,9-diene-17β,2'-thiolane]-3-one (21).

To 588 mg (1.15 mmol) of 15 in 10 mL of CH$_2$Cl$_2$ was added 1.5 mL of trifluoroacetic acid (TFA) and 0.5 mL of H$_2$O at 0° C. The reaction mixture was stirred at 0° C. for 30 min and then quenched with saturated NaHCO$_3$. The reaction mixture was extracted with CH$_2$Cl$_2$. The extract was washed with water, followed by brine. The organic layer was dried over anhydrous Na$_2$SO$_4$, filtered, concentrated and then chromatographed on silica gel with 6:3:1 EtOAc-hexane-MeOH as eluant to give 375 mg (70% yield) of 21 as a mixture of isomers. The two isomers were separated by preparative HPLC on a C-18 reverse phase column (YMC 250×20 mm I.D) and 65% methanol-water as eluent to give 180 mg of the major isomer and 130 mg of the minor isomer: $^1$H NMR (major) δ6.99 (d, 2, J=8.3 Hz, ArH), 6.65 (d, 2, J =8.5 Hz, ArH), 5.76 (s, 1, C-4 H), 4.35 (d, 1, J=6.2 Hz, C-11 H), 3.05 (m, 2, J=7.1 Hz, J=9.1 Hz, C-5' H), 2.90 (s, 6, N(CH$_3$)$_2$), 0.75 (s, 3, C-18 H); $^1$H NMR (minor) δ 7.03 (d, 2, J=8.3 Hz, ArH), 6.65 (d, 2, J=8.5 Hz, ArH), 5.76 (s, 1, C-4 H), 4.32 (d, 1, J=6.2 Hz, C-11 H), 2.90 (s, 6, N(CH$_3$)$_2$), 2.75 (t, 2, J=6.2 Hz), 0.96 (s, 3, C-18 H). Anal. (major isomer) Calcd for C$_{29}$H$_{39}$NSO$_2$.0.25 H$_2$O C, 73.69; H, 8.10; N, 2.96; S, 6.78. Found: C, 73.64; H, 8.00; N, 2.88; S, 6.58.

11β-{4-{1,1-[1,2-Ethanediylbis(oxy)]ethyl}phenyl}-3,3-[1,2-ethanediylbis(oxy)]-5α-hydroxy-1'-oxo-spiro[estr-9-ene-17β,2'-thiolane] (16).

To a solution of the Grignard reagent prepared from 1.74 g (7.12 mmol) of 4-{ 1,1-[1,2-ethanediylbis(oxy)]}phenyl bromide and 180 mg (7.47 mmol) of Mg in 7.16 mL of THF was added, at −20° C., 350 mg (3.56 mmol) of CuCl. To this was immediately added 700 mg (1.78 mmol) of the sulfoxide-epoxide 10 dissolved in 2 mL of THF. The reaction mixture was stirred at −20° C. for 30 min and then quenched with saturated NH$_4$Cl solution. The reaction mixture was extracted with EtOAc and the EtOAc layer was stirred for 3–4 h with a solution of 300 mL of saturated NH$_4$Cl to which was added 3 mL of 14.9 N aqueous NH$_4$OH. The organic layer was washed with water, followed by brine and dried over anhydrous Na$_2$SO$_4$. The EtOAc solution was filtered, concentrated and the residue chromatographed on silica gel with 6:3:1 EtOAc-hexane-MeOH as eluent to give 1.06 g (66% yield) of 16; $^1$H NMR δ7.40–7.32 (m, 2, ArH), 7.20–7.11 (m, 2, ArH), 4.41 (s, 1, C-5 OH), 4.32 (d, 1, J=6.8 Hz, C-11 H), 3.93–4.02 (m, 4, (OCH$_2$)$_2$), 3.71–3.76 (m, 4, (OCH$_2$)$_2$), 0.69 (s, 3, C-18 H, minor), 0.61(s, 3, C-18 H, major).

11β-(4-Acetylphenyl)-1'-oxo-spiro[estra-4,9-diene-17β,2'-thiolane]-3-one (22).

Ketal 16 was dissolved in 20 mL of CH$_2$Cl$_2$ and cooled to 0° C. To this was added 0.5 mL of water and 2 mL of TFA dropwise. The reaction mixture turned yellow. After being stirred at 0° C. for 1 h, the reaction was quenched by addition of saturated NaHCO$_3$ solution. The reaction mixture was extracted with 300 mL of CH$_2$Cl$_2$ and the extract was washed with water, followed by brine, and dried over anhydrous MgSO$_4$. The CH$_2$Cl$_2$ layer was filtered, concentrated and the crude product chromatographed on silica gel with 6:3:1.5 EtOAc-hexane-MeOH as eluent to give 80% yield of desired product. The two isomers were separated on a YMC C-18 reversed phase preparative HPLC column with 65% methanol-water as eluent to give 200 mg of pure major isomer 22a which had the following characteristics: mp 148–154° C.; $^1$H NMR δ7.90 (d, 2, J=8.1 Hz, ArH), 7.28 (d, 2, J=8.2 Hz, ArH), 5.81 (s, 1, C-4 H), 4.47 (d, 1, J=6.5 Hz, C-11 H), 2.69 (s, 3, COCH$_3$), 0.69 (s, 3, C-18 H); mass spectrum, m/z (rel intensity) 462 (6), 446 (56), 371 (25), 331 (24), 280 (66), 235 (25), 165 (100), 119 (50); Anal. Calcd for C$_{29}$H$_{34}$SO$_3$: C, 75.29; H, 7.41, S; 6.93. Found: C, 75.06; H, 7.66; S, 6.73.

3,3-[1,2-Ethanediylbis(oxy)]-5α-hydroxy-11β-[4-(methylthio)phenyl]-1'-oxo-spiro[estr-9-ene-17β,2'-thiolane] (17).

To a solution of the Grignard reagent prepared from 1.552 g (7.64 mmol) of 4-methylthiophenyl bromide and 193 mg (8.02 mmol) of Mg in 16.0 mL of THF, was added, at −20° C., 379 mg (3.83 mmol) of CuCl. To this was immediately added 750 mg (1.91 mmol) of the sulfoxide epoxide 10 dissolved in 4 mL of THF. The reaction mixture was stirred at −20° C. for 30 min and then quenched with saturated NH$_4$Cl solution. The reaction mixture was extracted with EtOAc and the EtOAc layer was stirred for 3–4 h with a solution of 300 mL of saturated NH$_4$Cl to which was added 3 mL of 14.9 N NH$_4$OH solution. The organic layer was then washed with water, followed by brine, and dried over anhydrous Na$_2$SO$_4$. The EtOAc solution was filtered, concentrated and the residue chromatographed on silica gel with 6:3:1 EtOAc-hexane-MeOH as eluent to give 650 mg (66% yield) of 17; $^1$H NMR δ7.26–7.07 (m, 4, ArH), 4.40 (s, 1, C-5 OH), 4.24 (d, 1, J=6.8 Hz, C-11 H), 3.93–4.02 (m, 4, (OCH$_2$)$_2$), 2.46 (s, 3, SCH$_3$), 0.86 (s, 3, C-18 H, minor), 0.66 (s, 3, C-18 H, major).

11β-[4-MethyIthio)phenyl]-1'-oxo-spiro[estra-4,9-diene-17β,2'-thiolane]-3-one (23).

Ketal 17 (650 mg, 1.26 mmol) was dissolved in 25 mL of CH$_2$Cl$_2$ and cooled to 0° C. To this solution was added 0.5 mL of water and 2 mL of TFA dropwise. The reaction mixture turned yellow. After being stirred at 0° C. for 1 h, the reaction was quenched by addition of saturated NaHCO$_3$ solution. The reaction mixture was extracted with 300 mL of CH$_2$Cl$_2$, and the extract was washed with water, followed by brine, and dried over anhydrous MgSO$_4$. The CH$_2$Cl$_2$ layer was filtered, concentrated and the crude product chromatographed on silica gel with 6:3:1.5 EtOAc-hexane-MeOH as eluent to give 85% yield of desired product. The two isomers were separated on a YMC reversed phase preparative HPLC column with 70% methanol-water to give 250 mg of pure major isomer 23a which had the following data: mp 160–163° C.; $^1$H NMR δ7.18 (d, 2, J=8.5 Hz, ArH), 7.08 (d, 2, J=8.4 Hz, ArH), 5.79 (s, 1, C-4 H), 4.39 (d, 1, J=6.4 Hz, C-11 H), 2.46 (s, 3, SCH$_3$), 0.73 (s, 3, C-18 H); mass spectrum, m/z (rel intensity) 466 (53), 448 (96), 375 (36), 283 (100), 235 (36), 191 (23), 137 (98), 91 (48); Anal. Calcd for C$_{28}$H$_{34}$S$_2$O$_2$: C, 72.06; H, 7.34, S; 13.74. Found: C, 71.93; H, 7.36; S, 13.73.

1',1'-Dioxo-3,3-[1,2-ethanediylbis(oxy)]-5,10α-oxido-spiro[estr-9(11)-ene-17β,2'-thiolane] (11).

To a solution of 120 mg (0.32 mmol) of diene ketal 9 in 0.5 mL of CH$_2$Cl$_2$ was added 37 mg of dibasic sodium hydrogen phosphate. This mixture was cooled to 0° C. and then 20 μL (0.14 mmol) of hexafluoroacetone trihydrate followed by 88 μL (1.53 mmol) of hydrogen peroxide was added. The reaction mixture was slowly warmed to room temperature and stirred for 2 days. The reaction was quenched with 5% Na$_2$SO$_3$ solution, extracted with CH$_2$Cl$_2$, and washed with water followed by brine. The organic layer was dried over anhydrous MgSO$_4$, filtered, concentrated, and the crude product chromatographed. Elution with 5:1 hexane-EtOAc gave 70 mg (52% yield) of 11. $^1$H NMR δ6.04 (d, 1, J=2.4 Hz, C-11 H), 3.94–3.88 (m, 4, (CH$_2$O)$_2$), 3.02 (t, 2, J=7.4 Hz, J=8.5 Hz, C-5 H), 1.14 (s, 3, C-18 H).

1',1'-Dioxo-11β-[4-(N,N-dimethylamino)phenyl]-3,3-[1, 2-ethanediylbis(oxy)]-5α-hydroxy-spiro[estr-9-ene-17β,2'-thiolane] (18).

A solution of the Grignard reagent was prepared from 360 mg (1.8 mmol) of p-bromo-N,N-dimethylaniline and 45 mg (1.87 mmol) of Mg in 2 mL of THF. The Grignard solution was cooled to −10° C. under an inert atmosphere. To the Grignard solution was added 35.5 mg (0.36 mmol) of CuCl followed by 50 mg (0.12 mmol) of epoxide 11 in 1 mL of THE. The reaction was stirred at −10° C. for 30 ml and then quenched with saturated NH$_4$Cl solution. The reaction mixture was extracted with EtOAc, washed twice with saturated NH$_4$Cl solution and dried over anhydrous Na$_2$SO$_4$. The EtOAc layer was filtered, concentrated, and chromatographed on silica gel with 2:1 EtOAc-hexane as eluent to give 42 mg (66% yield) of 18. $^1$H NMR δ6.99 (d, 2, J =8.6 Hz, ArH), 6.57 (d, 2, J =8.7 Hz, ArH), 4.35 (s, 1, C-5 OH), 4.18 (d, 1, J=6.0 Hz, C-11 H), 3.95–3.86 (m, 4, (CH$_2$O)$_2$), 2.91 (t, 2, J =7.0 Hz, J =9.0 Hz, C-5 H), 2.88 (s, 6, N(CH$_3$)$_2$), 0.71 (s, 3, C-18 H).

1',1'-Dioxo-11β-[4-(N,N-dimethylamino)phenyl]-spiro [estra-4,9-diene-17β,2'-thiolane]-3-one (24).

To 350 mg (0.65 mmol) of 18 in 5 mL of CH$_2$Cl$_2$ was added 1.5 mL of TFA and 0.5 mL of H$_2$O at 0° C. The reaction mixture was stirred at 0° C. for 30 min and then quenched with saturated NaHCO$_3$ solution. The reaction mixture was extracted with CH$_2$Cl$_2$, washed with water, followed by brine. The organic layer was dried over anhydrous Na$_2$SO$_4$, filtered, concentrated and then chromatographed on silica gel with 2:1 EtOAc-hexane as eluent to give 250 mg (80% yield) of 24: $^1$H NMR δ7.02 (d, 2, J=8.5 Hz, ArH), 6.65 (d, 2, J=8.9 Hz, ArH), 5.57 (s, 1, C-4 H), 4.36 (d, 1,J=6.2 Hz, C-11 H), 3.02 (t, 2,J=7.1 Hz, J=9.1 Hz, C-5 H), 2.90 (s, 6, N(CH$_3$)$_2$), 0.86 (s, 3, C-18 H); mass spectrum, m/z (rel intensity), 479 (M+, 28), 415 (3), 251 (3), 235 (2),121 (100), 91 (6).

1',1'-Dioxo-3,3-[1,2-ethanediylbis(oxy)]-5α-hydroxy-11β-[4-(methylthio)phenyl]-spiro[estr-9-ene-17β,2'-thiolane] (20).

To a solution of the Grignard reagent prepared from 1.446 g (7.13 mmol) of aryl halide and 180 mg (7.47 mmol) of Mg in 7.2 mL of THF, was added, at 0° C., 352 mg (3.56 mmol) of CuCl. To this was immediately added 750 mg (1.78 mmol) of the sulfone epoxide 11 dissolved in 8 mL of THF. The reaction mixture was stirred at 0° C. for 30 min and then quenched with saturated NH$_4$Cl solution. The reaction mixture was extracted with EtOAc and the EtOAc was stirred for 3–4 h with 300 mL of saturated NH$_4$Cl solution to which was added 3 mL of 14.9 N NH$_4$OH solution. The organic layer was then washed with water, followed by brine and dried over anhydrous Na$_2$SO$_4$. The EtOAc solution was filtered, concentrated and the residue chromatographed on silica gel with 2:1 EtOAc-hexane as eluent to give 650 mg (67% yield) of 20; $^1$H NMR δ7.14 (s, 4, ArH), 4.41 (s, 1, C-5 OH), 4.28 (d, 1, J=6.5 Hz, C-11 H), 3.90–4.02 (m, 4, (OCH$_2$)$_2$), 2.45 (s, 3, SCH$_3$), 0.76 (s, 3, C-18 H).

1',1'-Dioxo-11β-[4-(methylthio)phenyl]-spiro[estra-4,9-diene-17β,2'-thiolane]-3-one (26).

Ketal 20 (650 mg, 1.26 mmol) was dissolved in 25 mL of CH$_2$Cl$_2$ and cooled to 0° C. To this was added 0.5 mL of water and 2 mL of TFA dropwise. The reaction mixture turned yellow. After being stirred at 0° C. for 1 h the reaction was quenched by addition of saturated NaHCO$_3$ solution. The reaction mixture was extracted with 300 mL of CH$_2$Cl$_2$ and the extract was washed with water, followed by brine, and dried over anhydrous MgSO$_4$. The CH$_2$Cl$_2$ solution was filtered, concentrated and the crude product chromatographed on silica gel with 6:3:1.5 EtOAc-hexane-MeOH as eluent to give 85% yield of desired product: mp 242–248° C.; $^1$H NMR δ7.17 (d, 2,J=8.6 Hz, ArH), 7.10 ( d, 2, J=8.6 Hz, ArH), 5.77 (s, 1, C-4 H), 4.39 (d, 1, J=6.7 Hz, C-11 H), 2.47 (s, 3, SCH$_3$), 0.82 (s, 3, C-18 H); mass spectrum, m/z (rel intensity) 482 (100), 435 (20), 375 (11), 283 (23), 235 (19), 165 (37), 137 (78), 91 (50); Anal. Calcd for C$_{28}$H$_{34}$S$_2$O$_3$.0.25 H$_2$O: C, 69.03; H, 7.16, S; 13.16. Found: C, 69.09; H, 7.10; S, 12.92.

11β-[4-(N,N-Dimethylamino)phenyl]-spiro[estra-4,9-diene-17β,2'-thiolane]-3-one (12).

A solution of 250 mg (0.475 mmol) of sulfoxide 15 was prepared in 2 mL of anhydrous THF. The solution was cooled to 0° C. and was maintained under nitrogen. To this was added dropwise 0.95 mL of a I M solution of LAH in ether. After complete addition of the LAH, 1.05 mL of a 1 M solution of $TiCl_4$ in toluene was added dropwise. On addition of the $TiCl_4$ the solution turned black and a thick precipitate formed which was difficult to stir. More THF (1 mL) was added, and the reaction mixture was stirred at 0° C. for 45 min, and then at room temperature for 20 min. The reaction was quenched by addition of saturated $NH_4Cl$ solution. The reaction mixture was extracted with $CH_2Cl_2$ and the extract was washed with water followed by brine. The organic layer was concentrated and the crude product was dissolved in 25 mL of $CH_2Cl_2$. To this was added 0.5 mL of water and the mixture was cooled to 0° C. To the solution at 0° C. was added 1 mL of TFA dropwise. The reaction was stirred for 1 h and then quenched with saturated $NaHCO_3$ solution. The reaction mixture was extracted with $CH_2Cl_2$ and the extract was washed with water, followed by brine, and dried over anhydrous $Na_2SO_4$. The $CH_2Cl_2$ layer was filtered, concentrated and the crude residue chromatographed on silica gel with 2:1 hexane-EtOAc as eluent to give 107.5 mg (50.5% yield) of pure 12: mp 112–120° C.; $^1H$ NMR δ7.03 (d, 2, J=8.6 Hz, ArH), 6.66 (d, 2, J=8.8 Hz, ArH), 5.75 (s, 1, C-4 H), 4.38 (d, 1, J=6.4 Hz, C-11 H), 2.91 (s, 6, $N(CH_3)_2$), 0.61 (s, 3, C-18 H); mass spectrum, m/z (rel intensity) 447 (89), 280 (16), 134 (16), 121 (100); Anal. Calcd for $C_{29}H_{37}NSO$: C, 77.81; H, 8.33, N, 3.31, S, 7.16. Found: C, 77.74; H, 8.34; N, 3.31; S, 7.12.

11β-[4-(Methylthio)phenyl]-spiro[estra-4,9-diene-17β,2'-thiolane]-3-one (14).

A solution of 590 mg (1.12 mmol) of sulfoxide 17 was prepared in 28 mL of anhydrous THF. The solution was cooled to 0° C. and was maintained under nitrogen. To this was added dropwise 2.2 mL of a 1 M solution of LAH in ether. After complete addition of the LAH, 2.45 mL of 1 M solution of $TiCl_4$)in toluene was added dropwise. On addition of the $TiCl_4$ the solution turned black. The reaction mixture was stirred at 0° C. for 45 min, and then at room temperature for 20 min. The reaction was quenched by addition of saturated $NH_4Cl$ solution. This mixture was extracted with $CH_2Cl_2$ and washed with water, followed by brine. The organic layer was concentrated and the crude product was dissolved in 25 mL of $CH_2Cl_2$. To this was added 0.5 mL of water and to the solution at 0° C. was added 2 mL of TFA dropwise. The reaction mixture was stirred for 1 h and then quenched with saturated $NaHCO_3$ solution. This mixture was extracted with $CH_2Cl_2$, washed with water, followed by brine, and dried over anhydrous $Na_2SO_4$. The $CH_2Cl_2$ layer was filtered, concentrated and the crude product chromatographed on silica gel with 2:1 hexane-EtOAc as eluent to give 330 mg (65% yield) of 14. mp 108–110° C.; $^1H$ NMR δ7.18 (d, 2, J=8.6 Hz, ArH), 7.10 (d, 2, J=10.6 Hz, ArH), 5.78 (s, 1, C-4 H), 4.40 (d, 1, J=6.4 Hz, C-11 H), 2.46 (s, 3, $ArSCH_3$), 0.57 (s, 3, C-18 H); mass spectrum, m/z (rel intensity) 450 (100), 375 (9), 350 (27), 335 (33), 235 (34), 211 (46), 137 (50), 100 (48), 91 (29), 79 (19); Anal. Calcd for $C_{28}H_{34}S_2O$: C, 74.62; H, 7.60; S, 14.23. Found: C, 74.55; H, 7.73; S, 14.25.

Biological Information

The biological activity of the compounds of this invention was examined by means of whole cell receptor binding studies.

Receptor Binding. The affinity of the compounds for hormone receptors was determined by standard procedures similar to those that have been described, inter alia, by Wagner et al., *Proc. Natl. Acad. Sci.,* 93, 8739–8744 (1996) for COS-1 cells. The human breast carcinoma (T-47D) cell line was used to assess RBA for progestin receptor. The cell line used was obtained from ATCC (American Type Culture Collection) and stored frozen at −135° C. until a week before the assays were conducted. The cells were thawed and cultured to achieve the desired cell number (5 to 7 days on average). They were maintained at 37° C. with growth media until they were 90–100% confluent, at which time they were recovered from the growth flasks and dispersed into individual wells of a 12-well tissue culture plate at a count of 4×105 cells in one mL medium per well. After 24 h the cells adhered to the bottom of the 12-well plates. At this point, the receptor binding assay procedure was initiated by the addition of test or standard compounds with 3H-R5020 (promegestone). After incubation overnight, medium was removed, the cells were washed and solubilized and radioactivity was measured by liquid scintillation spectrometry. Nonspecific binding was determined by incubation with excess of unlabeled R5020 and subtracted from total binding to calculate specific binding. The progesterone binding assay was conducted with several concentrations of the reference standard (promegestone, R-5020) and an internal standard (progesterone). These hormones were allowed to compete with tritiated competitor (3H-promegestone, 3H-R5020) to estimate relative binding. Test steroids were tested at three or more concentrations between 0.01 to 1000 nM. If 50% displacement of the 3H-R5020 from the receptor was not achieved by the unknown, higher or lower concentrations were tested, as needed, to obtain that goal. All compounds were tested in duplicate for at least two assays. The percentage of specifically bound 3H-R5020 for each concentration tested was calculated and binding curves were generated by plotting the percentage of specifically bound 3H-R-5020 versus the concentration of the competitor. The relative binding activity (RBA) of the test compounds, relative to the reference standard (R5020) as well as the internal standard, was determined from the ratio of concentrations causing 50% displacement for each unknown and standard and expressed as a percentage value. These concentrations were obtained by graphical interpolation of the plots. When this was done, the results shown in Table 1 were obtained.

TABLE 1

Binding to Human Progestin Receptor in T47-D Cells

| Compound | Aryl Substituent | 17,17 subst. | $IC_{50}$ (nM) | Relative Binding[a] % R5020 | % Prog. |
|---|---|---|---|---|---|
| 12 | $Me_2N$ | spirothiolane | 2.8 | 105 | 983 |
| 21a[b] | $Me_2N$ | spirothiolane oxide | 3.1 | 128 | 825 |
| 14 | MeS | spirothiolane | 4.1 | 49 | 651 |
| 21b[c] | $Me_2N$ | spirothiolane oxide | 6.6 | 43 | 260 |
| 24 | $Me_2N$ | spirothiolane dioxide | 13 | 29 | 199 |
| 22b[c] | $CH_3CO$ | spirothiolane oxide | 135 | 2 | 25 |
| 22a[b] | $CH_3CO$ | spirothiolane oxide | 183 | 2 | 19 |

[a]Relative binding was compared in the same assay. Thus relative binding % rankings may not exactly correlate with the $IC_{50}$ rankings.
[b]Major isomer
[c]Minor isomer

Smith et al. (*Journal Biological Chemistry.* 1974; 249(18):5924–5932) report that 17-thiomethylandrost- 4-en-3-one binds to the human progestin receptor with 25% the affinity of progesterone. Compounds of the current invention have much stronger binding than that (see Table 1 above).

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A hormonal or antihormonal steroid compound of structure I (I)

wherein s is an integer from 0 to 2;

$R^1$ is 4-$(R^2R^3N(O)_r)$-, where r is 0 or 1 and $R^2$ and $R^3$ are each independently H, $C_{1-6}$ alkyl, $C_{3-8}$ cycloalkyl, $C_{2-6}$ alkenyl or $C_{2-6}$ alkynyl, any of which may be optionally substituted; or where q is 0 or 1 and Y is —$(CH_2)_m$- where m is an integer of 0 to 5, or Y is —$(CH_2)_n$-Z—$(CH_2)_p$- where n is an integer of 0 to 2, p is an integer of 0 to 2 and Z is a heteroatom (optionally substituted) and where the methylene groups in both cases may be optionally substituted; or $R^1$ is 4-halo-, 4-HO—, 4-$CF_3SO_2O$—, 4-$CH_3O$—, 4-$CH_3S$—, 4-$CH_3S(O)$—, 4-$CH_3S(O)_2$—, 4-$CH_3CO$—, 4-$CH_3CH(OH)$—, 4-N≡C—, 4-HC≡C—, 4-$C_6H_5C≡C$—, 4-$H_2C=CH$—, 4-$C_2H_5$—, 4-MeC(=$CH_2$)—, 4-$C_6H_5$, 4-(N-imidazolyl)-, 4-(N-pyrrolyl)-, 4-(2'-furyl), 4-(3'-furyl), 4-(2'-thiophenyl), 4-(3'-thiophenyl)-, 4-(2'-pyridyl), 4-(3'-pyridyl), 4-(4'-pyridyl)-, 4-(2'-thiazolyl)-, 4(2'-N-methylimidazolyl)-, or 4-(5'-pyrimidinyl)-;

$R^{14}$ is H or halo; or

$R^1$ and $R^{14}$ combine to form a ring where W is CH, $CH_2$, N, NH, O, or S, and $R^4$ is H, $CH_3$, or $C_2H_5$;

X is O or $NOR^5$, where $R^5$ is H or $C_{1-6}$ alkyl, $C_{3-8}$ cycloalkyl, $C_{2-6}$ alkenyl, $C_{2-6}$ alkynyl, $C_{6-12}$ aryl, or heteroaryl, any of which may be optionally substituted; or X is (H,H), (H,OH) or X is (H,OSi($C_{1-6}$-alkyl)$_3$) or X is (H,$OCOR^5$), where $R^5$ is $C_{2-6}$ alkyl, $C_{3-8}$ cycloalkyl, $C_{2-6}$ alkenyl, $C_{2-6}$ alkynyl, $C_{6-12}$ aryl, aralkyl, aralkenyl, aralkynyl, heteroaryl, heteroaralkyl, heteroaralkenyl or heteroaralkynyl, any of which may be optionally substituted; or where Y is —$(CH_2)_m$- where m is an integer of 0 to 3, or Y is —$(CH_2)_n$-Z—$(CH_2)_p$- where n is an integer of 0 to 2, p is an integer of 0 to 2 and Z is a heteroatom (optionally substituted) or Z is a carbon atom substituted with one or two lower alkyl groups;

$R^6$ is H, $C_{1-6}$ alkyl, or halogen;

$R^8$ and $R^9$ are individually H, $C_{1-18}$ alkyl, $C_{2-18}$ alkenyl, $C_{2-18}$ alkynyl, $C_{4-8}$ cycloalkyl, $C_{6-12}$aryl, aralkyl, aralkenyl or aralkynyl, heteroaryl, heteroaralkyl, heteroaralkenyl or heteroaralkynyl, any of which may be optionally substituted; and $R^{10}$ is H, $C_{1-18}$ alkyl, $C_{2-18}$ alkenyl, $C_{2-18}$ alkynyl, $C_{4-8}$ cycloalkyl, $C_{6-12}$ aryl, aralkyl, aralkenyl or aralkynyl, heteroaryl, heteroaralkyl, heteroaralkenyl or heteroaralkynyl, any of which may be optionally substituted; and $R^{11}$ and $R^{12}$ are =$CH_2$ or $R^{11}$ and $R^{12}$ are each H;

pharmaceutically acceptable salts thereof.

2. The steroid having structure I of claim 1, wherein:

s is an integer from 0 to 2;

$R^1$—Ph is 4-aminophenyl, 4-(N-methylamino)phenyl, 4-(N,N-dimethylamino)phenyl, 4-(N-piperidino)phenyl, 4-(N-pyrrolidino)phenyl, 4-(N-morpholino)phenyl;

$R^{14}$ is H or $R^1$ and $R^{14}$-Ph is 1-methylindol-5-yl or 1-methyl-2,3-dihydroindol-5-yl;

X is O, NOH, or $NOCH_3$;

$R^6$ is H, $CH_3$, F or Cl;

$R^8$ is H, $CH_3$, or $C_6H_5$;

$R^9$ is H, $CH_3$, or $C_6H_5$;

$R^{10}$ is H, $CH_3$, or $C_6H_5$; and $R^{11}$ and $R^{12}$ are each H.

3. The steroid of claim 1, selected from the group consisting of

11β-(4-(N-methylamino)phenyl)-spiro[estra-4,9-diene-17β,2'-thiolane]-3-one;
11β-(4-(N,N-dimethylamino)phenyl)-spiro[estra-4,9-diene-17β,2'-thiolane]-3-one;
11β-(4-(N-piperidino)phenyl)-spiro[estra-4,9-diene-17β,2'-thiolane]-3-one;
11β-(4-(N-pyrrolidino)phenyl)-spiro[estra-4,9-diene-17β,2'-thiolane]-3-one;
11β-(4-(N-morpholino)phenyl)-spiro[estra-4,9-diene-17β,2'-thiolane]-3-one;
11β-(4-(N-methylamino)phenyl)-2'-oxospiro[estra-4,9-diene-17β,2'-thiolane]-3-one;
11β-(4-(N,N-dimethylamino)phenyl)-2'-oxospiro[estra-4,9-diene-17β,2'-thiolane]-3-one;
11β-(4-(N-piperidino)phenyl)-2'-oxospiro[estra-4,9-diene-17β,2'-thiolane]-3-one;
11β-(4-(N-pyrrolidino)phenyl)-2'-oxospiro[estra-4,9-diene-17β,2'-thiolane]-3-one;
11β-(4-(N-morpholino)phenyl)-2'-oxospiro[estra-4,9-diene-17β,2'-thiolane]-3-one;
11β-(4-(N-methylamino)phenyl)-2',2'-dioxospiro[estra-4,9-diene-17β,2'-thiolane]-3-one;
11β-(4-(N,N-dimethylamino)phenyl)-2',2'-dioxospiro[estra-4,9-diene-17β,2'-thiolane]-3-one;
11β-(4-(N-piperidino)phenyl)-2',2'-dioxospiro[estra-4,9-diene-17β,2'-thiolane]-3-one;
11β-(4-(N-pyrrolidino)phenyl)-2',2'-dioxospiro[estra-4,9-diene-17β,2'-thiolane]-3-one;
11β-(4-(N-morpholino)phenyl)-2',2'-dioxospiro[estra-4,9-diene-17β,2'-thiolane]-3-one.

4. A method of therapeutically treating the activity of progesterone comprising administering a therapeutically effective amount of the compound of claim 1, to a patient in need thereof for a therapeutic purpose.

5. The method of claim 4, wherein said therapeutic purpose is the treatment of endometriosis or uterine fibroids.

6. The method of claim 4, wherein said therapeutic purpose is cervical ripening preparatory to labor and delivery of offspring.

7. The method of claim 4, wherein said therapeutic purpose is the control or regulation of fertility.

8. The method of claim 4, wherein said therapeutic purpose is hormone replacement therapy.

9. The method of claim 4, wherein said therapeutic purpose is the treatment of tumors or cancers.

10. A method of forming a $C_{17}$ cyclic spirothiolane of a steriod compound (V) comprising:

i) reacting a $C_{17}$ thioketone (II) with an allylic organometalic compound (III); and ii) cyclizing an allylic thiol (IV) under free radical conditions, where $R^8$ and $R^9$ are individually H, $C_{1-18}$ alkyl, $C_{2-18}$ alkenyl, $C_{2-18}$ alkynyl, $C_{4-8}$ cycloalkyl, $C_{6-12}$ aryl, aralkyl, aralkenyl or aralkynyl, heteroaryl, heteroaralkyl, heteroaralkenyl or heteroaralkynyl, any of which may be optionally substituted; and $R^{10}$ is H, $C_{1-18}$ alkyl, $C_{2-18}$ alkenyl, $C_{2-18}$ alkynyl, $C_{4-8}$ cycloalkyl, $C_{6-12}$ aryl, aralkyl, aralkenyl or aralkynyl, heteroaryl, heteroaralkyl, heteroaralkenyl or heteroaralkynyl, any of which may be optionally substituted; and $R^{11}$ and $R^{12}$ are =$CH_2$ or $R^{11}$ and $R^{12}$ are each H; and M is a metal cation.

* * * * *

UNITED STATES PATENT AND TRADEMARK OFFICE
CERTIFICATE OF CORRRECTION

PATENT NO. : 6,043,235
DATED : March 28, 2000
INVENTOR(S) : Cook et al.

It is certified that error appears in the above-identified patent and that said Letters Patent is hereby corrected as shown below:

On the title page, insert the following under item [56],

U. S. PATENT DOCUMENTS

| EXAMINER INITIAL | | PATENT NUMBER | | | | | | ISSUE DATE | PATENTEE | CLASS | SUBCLASS | FILING DATE IF APPROPRIATE |
|---|---|---|---|---|---|---|---|---|---|---|---|---|
| | | 4 | 4 | 8 | 1 | 1 | 4 | 4 | 11/06/84 | Varma | | | |
| | | 4 | 5 | 2 | 9 | 5 | 4 | 8 | 07/16/85 | Varma ET AL. | | | |

Signed and Sealed this

Fifth Day of September, 2000

*Attest:*

Q. TODD DICKINSON

*Attesting Officer*   *Director of Patents and Trademarks*

UNITED STATES PATENT AND TRADEMARK OFFICE
CERTIFICATE OF CORRECTION

PATENT NO.   : 6,043,235                                           Page 1 of 1
DATED        : March 28, 2000
INVENTOR(S)  : C Edgar Cook et al.

It is certified that error appears in the above-identified patent and that said Letters Patent is hereby corrected as shown below:

Column 21,
Line 58, "4-N-C-" should read -- 4-N≡C- --.

Column 22,
Line 17, "$C_{2-6}$ alkyl" should read -- $C_{1-6}$ alkyl --.

Column 23,
Lines 12-13, "11β-(4-(N-methylamino)phenyl)-2 '-oxospiro[estra-4,9-diene- 17β,2'-thiolane]-3-one;" should read -- 11β-(4-(N-methylamino)phenyl)-2'-oxospiro[estra-4,9-diene-17β,2'-thiolane]-3-one; --.
Lines 25-26, "11β-(4-(N,N-dimethylamino)phenyl)-2',2'-dioxospiro[estra-4,9-diene-17β,2'-thiolane] -3-one;" should read -- 11β-(4-(N,N-dimethylamino)phenyl)-2',2'-dioxospiro[estra-4,9-diene-17β,2'-thiolane] -3-one; --.

Signed and Sealed this

First Day of June, 2004

JON W. DUDAS
*Acting Director of the United States Patent and Trademark Office*